United States Patent [19]
Matsumura et al.

[11] Patent Number: 5,753,110
[45] Date of Patent: May 19, 1998

[54] BIOCHEMICAL REACTOR OF LIQUID CURRENT TYPE, GROUNDWATER AND WASTEWATER PURIFYING SYSTEM EQUIPPED THEREWITH, AND LIQUID TRANSPORT-STIRRING APPARATUS THAT EMPLOYS THE TRANSPORT MEANS USED IN SAID REACTOR AND SYSTEM

[75] Inventors: Masatoshi Matsumura, Tsukuba; Naoyuki Fujii, Fukui; Yoshimi Imaida, Ichinomiya, all of Japan

[73] Assignee: Biomaterial Co., Ltd., Fukui, Japan

[21] Appl. No.: 658,847

[22] Filed: May 31, 1996

[51] Int. Cl.$^6$ ............................................. C02F 3/08
[52] U.S. Cl. ...................... 210/150; 210/251; 210/512.1; 210/619; 210/787
[58] Field of Search ........................ 210/619, 787, 210/150, 151, 251, 903, 512.1

[56] References Cited

U.S. PATENT DOCUMENTS

| | | |
|---|---|---|
| 4,157,303 | 6/1979 | Yoshikawa et al. ............ 210/150 |
| 4,268,385 | 5/1981 | Yoshikawa et al. ............ 210/150 |
| 4,726,686 | 2/1988 | Wolf et al. .................... 210/512.1 |
| 4,939,087 | 7/1990 | Van Wie et al. ................ 210/787 |
| 4,956,082 | 9/1990 | Choi ............................. 210/619 |
| 5,211,844 | 5/1993 | Hattori et al. .................. 210/151 |
| 5,240,599 | 8/1993 | Kew et al. ..................... 210/787 |
| 5,611,926 | 3/1997 | Nishida ......................... 210/787 |

FOREIGN PATENT DOCUMENTS

| | | |
|---|---|---|
| 02-138960 | 5/1990 | Japan . |
| 03-290443 | 12/1991 | Japan . |
| 07-196846 | 8/1995 | Japan . |

*Primary Examiner*—Thomas G. Wyse
*Attorney, Agent, or Firm*—Morrison & Foerster, LLP

[57] ABSTRACT

A liquid current type biochemical reactor and methods of use thereof are provided. The reactor is useful in purifying groundwater and wastewater by the process of biodegradation. Also provided is a liquid transport-stirring apparatus for use in biochemical reactors which transports and stirs large amounts of fluids with a small driving force.

42 Claims, 21 Drawing Sheets

BIOCHEMICAL REACTOR OF LIQUID CURRENT TYPE, GROUNDWATER AND WASTEWATER PURIFYING SYSTEM EQUIPPED THEREWITH, AND LIQUID TRANSPORT-STIRRING APPARATUS THAT EMPLOYS THE TRANSPORT MEANS USED IN SAID REACTOR AND SYSTEM

FIELD OF THE INVENTION

The present invention provides a biochemical reactor of liquid current type and methods of use thereof. More specifically, the biochemical reactor of this invention uses microorganisms (such as protozoa, mold, actinomycetes, yeast, and bacteria) which selectively remove or convert specific elements or compounds from groundwater and wastewater by the process of biodegradation.

The present invention also provides an apparatus for transporting and stirring fluids for use in the biochemical reactor. This apparatus transports and stirs large amounts of fluid, including liquid, gas, and solid-containing liquid, with a small driving force.

BACKGROUND OF THE INVENTION

Conventional liquid current biochemical reactors consist of a vessel to hold a raw liquid and a carrier on which microorganisms are immobilized. The microorganisms on the carrier biodegrade specific elements found in the vessel's raw liquid. The raw liquid is stirred by an impeller so that the liquid comes into uniform contact with the carrier and biodegradation can occur.

Reactors using microorganisms are termed "bioreactors" because these microorganisms perform highly specific, biological reactions. Bioreactors are typically used in the production of alcohol and antibiotics using cultured microorganisms, and in the removal of nitrogen and other specific elements from groundwater and wastewater. Because contamination of groundwater with chemical fertilizes is a serious problem, attention has recently focused on using bioreactors for the denitrification of groundwater.

Since the microorganisms are essential to the function of a bioreactor, it is important that the stirring required for uniform dispersion of carrier and uniform flow of liquid in the vessel does not break the carrier on which the microorganisms are attached.

Conventional bioreactors, as described above, use an impeller that exerts shear stress on the carrier. In addition, known bioreactors have difficulty maintaining uniform dispersion of the carrier in the raw liquid in the vessel because the carrier floats when their immobilized microorganisms emit a gas, thereby reducing the apparent specific gravity of the carrier. In order to address this problem, Japanese Patent Kokai No. 138960/1990 discloses a bioreactor as shown in FIG. 24. This apparatus comprises a vessel (101) that has two spaces therein separated horizontally by a filter (100). The vessel (101) holds a raw liquid (104) and a carrier (103) having immobilized microorganisms thereon. On the side wall of the vessel (101) is a circulating pipe (105) which discharges the raw liquid (together with the carrier) from the outlet near the surface of the raw liquid and returns it to the vessel through the inlet near the top of the filter (100). The circulating pipe (105) is provided with a liquid current jet mechanism (106). A circulating pump (107) pressurizes treated liquid (free of the carrier) discharged from the bottom of the vessel and feeds the liquid into the jet mechanism (106), thereby producing a jet. The resulting jet generates an upward swirl in the vessel which stirs the raw liquid and carrier.

Because stirring is accomplished by liquid current flow and not by an impeller, this bioreactor reduces the problem of carrier breakage. Further, in this design, accumulation of the carrier near the surface of the raw liquid is reduced because the carrier that would float is transported to the bottom of the vessel.

Nevertheless, the jet mechanism bioreactor has several important disadvantages. Because the jet mechanism is supplied by the treated liquid free of the carrier, a filter (100) must be provided. The necessity of a filter (100) makes this bioreactor difficult to construct and creates problems with clogging and maintenance. In addition, the jet mechanism requires a large capacity circulating pump to treat a large amount of raw liquid. Thus, large-scale jet mechanism bioreactors are difficult and expensive to construct. Furthermore, although the jet flow is less liable to damage the carrier than the impeller, breakage of the carrier still occurs due to the high velocity, high pressure jet flow used in this apparatus.

SUMMARY OF THE INVENTION

The present invention eliminates the disadvantages found in the conventional technology described in the preceding section. An object of the present invention is to provide a means to circulate and transport a large amount of raw liquid and carrier slowly using a low-power drive unit without damaging the carrier. Another object of the present invention is to provide a liquid current biochemical reactor using this transport means. Another object of the present invention is to provide a system for purifying groundwater and wastewater using the biochemical reactor. Furthermore, another object of the present invention is to provide a general-purpose apparatus for transporting and stirring liquids using the transport means. This apparatus is capable of transporting and stirring a large amount of liquid slowly using a low-power driving unit.

The present invention comprises an entirely new transport means for use in a liquid current biochemical reactor.

One embodiment of the present invention provides a biochemical reactor of liquid current type comprising: a vessel to hold an immobilizing carrier; a raw liquid and a transport means to transport the immobilizing carrier and the raw liquid over a certain distance within the vessel, wherein the transport means includes a rotary drive; a tubular centrifugal force generator which is turned by the rotary drive and has a suction passage extending outward from the axis of rotation and terminating with an outlet; and a tubular fluid guide which has an inlet at one end thereof and an internal passage extending from the inlet and communicating with the suction passage of the centrifugal force generator, wherein the inlet of the fluid guide and the outlet of the centrifugal force generator are positioned apart in the vessel.

The inlet of the fluid guide and the outlet of the centrifugal force generator are positioned according to the direction in which the fluid is transported. They may be positioned apart vertically in the vessel, for instance, where there is a difference in specific gravity between the carrier and the raw liquid and the carrier is likely to float or precipitate.

Where the carrier tends to float because it has a lower specific gravity than the raw liquid, it is preferred that the upper part of the vessel be tapered and the inlet of the fluid guide be positioned in the confined space where the carrier accumulates.

The inlet of the fluid guide may be stationary or vertically movable by an adjustable means.

The fluid guide, which leads the fluid to the centrifugal force generator, may be positioned such that its axis aligns with the shaft of the rotary drive.

The centrifugal force generator and the fluid guide may be integrally formed from a single tube, so that they are turned together. Alternatively, they may be formed separately and rotatably joined together, so that the centrifugal force generator is turned alone.

The centrifugal force generator may be enclosed by a hollow cylindrical casing which reduces fluid resistance during rotation. The hollow cylindrical casing has approximately the same radius as the maximum radius of rotation of the centrifugal force generator. It also has an opening in its circumferential wall, which communicates with the outlet of the centrifugal force generator.

The raw liquid may be fed to and discharged from the vessel intermittently or continuously. The vessel may also be provided with a means to feed the raw liquid continuously and to discharge the treated liquid continuously.

The biochemical reactor of liquid current type in the present invention may be used alone or in series. When used in series, two or more units of the reactor may be placed side by side or on top of the other and arranged so that the treated liquid discharged from the preceding unit is fed into the following unit.

The biochemical reactor in the present invention can be used regardless of whether the apparent specific gravity of the immobilizing carrier is greater or smaller than that of the raw liquid. Despite the tendency of the carrier to float as it decreases in apparent specific gravity when the immobilized microorganisms emit a gas, the subject invention smoothly introduces the immobilizing carrier into the lower part of the vessel, thereby uniformly dispersing the carrier in the vessel.

The biochemical reactor of the present invention may be used for denitrification or methane fermentation if the carrier supports denitrifying bacteria or methane-generating bacteria, respectively. It may also be used for reducing the level of ammonium nitrogen or BOD (biochemical oxygen demand) if the immobilizing carrier supports nitrifying bacteria or microorganisms living in activated sludge.

As described above, the biochemical reactor of the present invention is most suitable for applications where the immobilizing carrier is used; however, it may also be used for applications where an immobilizing carrier is not employed.

The biochemical reactor of the present invention may be incorporated into existing water purification facilities made up of sedimentation basins, filter tanks, and chemical treatment tanks, and the like.

The transport means used in the above-mentioned biochemical reactor may be applied to other purposes or to the general-purpose fluid transport-stirring apparatus. This apparatus is made up of a rotary drive means and a centrifugal force generator. The centrifugal force generator includes a suction passage along the axis of rotation, a tube extending outward from the axis of rotation and an outlet at the end of the tube. The centrifugal force generator is immersed in the vessel holding a fluid.

The biochemical reactor of liquid current type according to the present invention is designed to selectively remove and convert specific elements and compounds contained in the raw liquid using microorganism, cells, or enzymes immobilized on a carrier. The microorganisms proliferate as they capture specific elements or compounds in the raw liquid, and the raw liquid is freed of specific elements and compounds. Examples of elements to be removed or converted include, but are not limited to, nitrogen, methane or ammonia nitrogen.

The immobilizing carrier is circulated together with the raw liquid in the reactor. This circulation takes place as described below. In the following explanation, the terms "raw liquid" and "fluid" are used interchangeably.

The carrier supporting the microorganisms floats, precipitates, or suspends in the raw liquid, depending on its specific gravity in relation to that of the raw liquid. The carrier is drawn into the fluid guide through its suction inlet which is positioned where the carrier accumulates. The fluid guide then delivers the carrier to the tubular centrifugal force generator.

During rotation, the centrifugal force generator exerts centrifugal force on the fluid passing through it and the fluid is discharged from the outlet of the centrifugal force generator. The same amount of fluid discharged is concurrently taken into the fluid guide through its suction inlet. Accordingly, the fluid is transported from one place to another in the vessel. The transport of fluid brings about stirring because the fluid is discharged as the outlet turns about the axis of rotation.

Except for a shaft to transmit rotary motion, the fluid passage in the centrifugal force generator has no mechanical parts. Thus, large amounts of fluid can be transported without causing any damage to the fluid passage.

The centrifugal force generator turns at a relatively low speed. In addition, it has no sharp edges like an impeller. Therefore, it does not harm the carrier suspended in the surrounding liquid. The centrifugal force generator requires only a small driving power, for example, a small drive unit.

When the carrier supporting microorganisms and the raw liquid have different specific gravities, the carrier will tend to float or precipitate. The suction inlet of the fluid guide, positioned where the carrier accumulates, transports floating carrier downward in the vessel and the precipitating carrier upward in the vessel, thereby providing uniform distribution.

According to another aspect of the invention, the suspended carrier is uniformly collected from the area surrounding the suction inlet and then introduced into the fluid guide.

According to another aspect of the invention, the suction inlet is movable up and down in relation to the level of the raw liquid, thereby controlling the amount of carrier drawn into the inlet.

According to another aspect of the invention, the axis of the fluid guide tube is aligned with the shaft of the rotary drive. In this embodiment, the fluid guide does not exert centrifugal force on the fluid passing through it and, therefore, does not prevent the fluid from being discharged by centrifugal force generated by the centrifugal force generator.

According to another aspect of the invention, the centrifugal force generator and the fluid guide are integrally constructed of a single tube thereby rotating together.

According to another aspect of the invention, the centrifugal force generator and the fluid guide are rotatably joined to each other and only the centrifugal force generator rotates.

According to another aspect of the invention, the centrifugal force generator is enclosed by a hollow cylindrical casing, which has approximately the same radius as the maximum radius of its rotation and also has an opening in its circumferential wall, which communicates with its outlet. The hollow casing, which is capable of rotating together with the centrifugal force generator, reduces resistance during rotation because of has a symmetry of rotation, and, consequently, the rotary drive unit needs only supply a small amount of power.

According to another aspect of the invention, two or more units of the biochemical reactor of liquid current type are arranged side by side or on top of each other so that the raw liquid is treated in multiple stages. In this embodiment, efficiency of treatment may be increased because the raw liquid is circulated less frequently in each unit.

The biochemical reactor of liquid current type according to the present invention may also be employed to handle a raw liquid without a carrier. In this embodiment, a large amount of liquid may be transported slowly using only a small amount of electric power.

The above-mentioned biochemical reactor of liquid current type may be combined with existing water purification facilities such as sedimentation basins, filter tanks, and chemical treatment tanks, and the like, to remove or convert specific elements (such as nitrogen) and compounds and BOD which remain unaffected in conventional purification systems.

Applying the above-described transport means to the liquid transport-stirring apparatus results in the centrifugal force generator exerting a centrifugal force on the fluid passing through it. As a result, the fluid is discharged from the outlet and drawn into the suction passage. Since the fluid is discharged as the outlet turns, simultaneous transport and stirring of the fluid occurs.

Except for a shaft to transmit rotary motion, the fluid passage in the centrifugal force generator lacks mechanical parts. Consequently, a large amount of fluid can be transported without causing damage to any solids which might be in the fluid.

The centrifugal force generator rotates at a relatively low speed and lacks sharp edges like an impeller. Therefore, the solids in suspension around it are not damaged and only a small driving power is required for its operation.

DESCRIPTION OF THE PREFERRED EMBODIMENTS

The present invention will be described in more detail with reference to the examples illustrated in the accompanying drawings.

Figure 1:
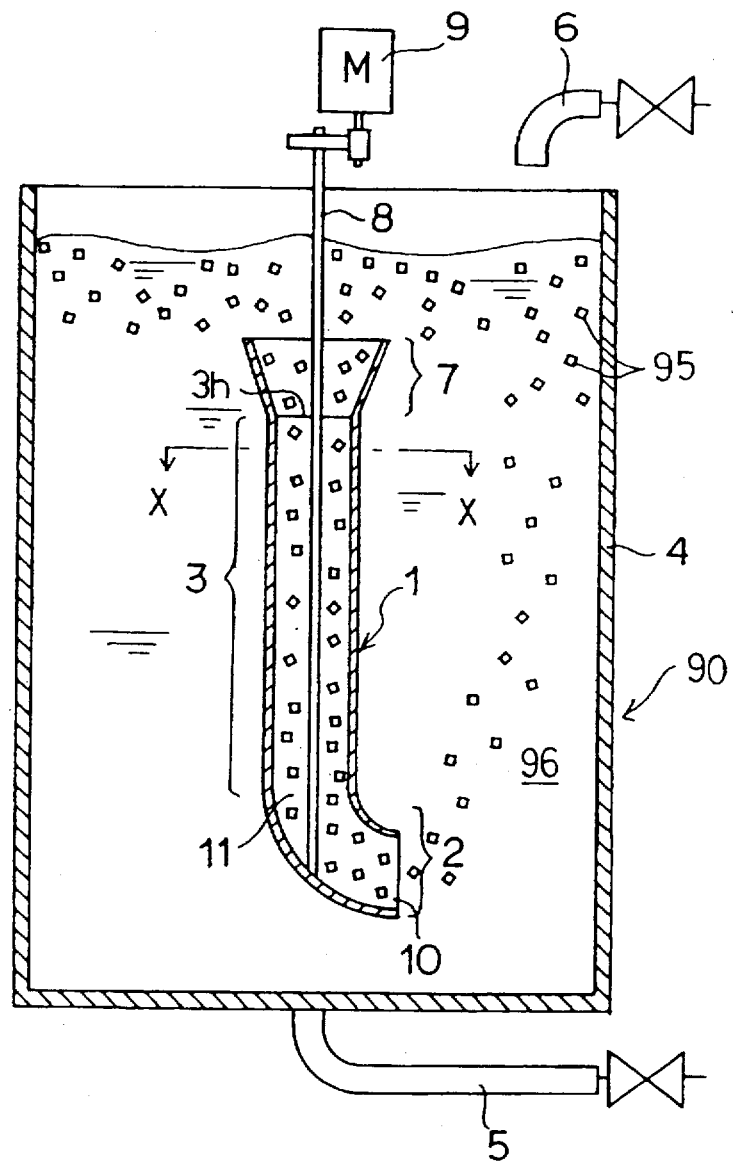
FIG. 1 is a sectional view of one example illustrating the basic structure of the biochemical reactor of liquid current type according to the present invention.
Figure 2:
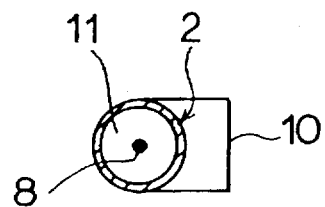
FIG. 2 is a sectional view taken along the line X—X in FIG. 1.

FIG. 1 is a vertical sectional view of one embodiment which illustrates the basic structure of the biochemical reactor of liquid current type according to the present invention. FIG. 2 is a sectional view taken along the line X—X in FIG. 1.

The biochemical reactor in this embodiment comprises a vessel (4) and a transport tube (1) placed therein. The vessel (4) holds a raw liquid (96) containing an immobilizing carrier (95) which supports microorganisms thereon. The transport tube (1) is rotated by a rotary drive (9), for example, an electric motor.

A discharge tube (5) is provided at the bottom of the vessel, through which the treated liquid is discharged. A feed tube (6) is also provided at the top of the vessel, through which the vessel is supplied with the raw liquid. The discharge tube (5) and the feed tube (6) may be at different positions. For example, the discharge tube may be attached to the side wall of the vessel and a drain may be attached to the bottom of the vessel so that precipitates are discharged through it.

The carrier (95) may be, for example, the type disclosed in Japanese Patent Laid-open No. 290443/1991 or the open-cell foam of a cellulose compound resistant to biodegradation proposed in Japanese Patent Application No. 351234/1993. Preferably, the carrier has a particle diameter of 0.5 to 50 mm and a pore diameter smaller than 2000 μ. The carrier may be cubic, rectangular parallelepipedic, columnar, or non-cylindrical in shape. The carrier is not limited to an open-cell foam of cellulose. It may be a porous and made of materials other than cellulose or it may be gel-like, made from calcium alginate or -carrageenan.

The carrier may support, for example, microorganisms, cells, or enzymes. Microorganisms may be either anaerobic bacteria or aerobic bacteria. Anaerobic bacteria include denitrifying bacteria and aerobic bacteria include nitrifying bacteria or microorganisms and protozoa living in activated sludge.

Examples of the denitrifying bacteria include the genera of Pseudomonas, Micrococcus, Spirillum, Achromobacter, Alcaligenes, and Hyphomicrobium.

Examples of the nitrifying bacteria include nitrate oxidizing bacteria belonging to the genera of Nitrobacter and Nitrococcus and nitrite oxidizing bacteria belonging to the genera of Nitrosomonas and Nitrosococcus.

Examples of the microorganisms living in activated sludge include the genera of Pseudomonas, Klebsiella, Micrococcus, and Microbacterium.

Examples of the protozoa living in activated sludge include the genera of Zoogloea, Vorticella, and Epistilis.

Examples of other microorganisms include those which generate methane gas.

Depending on the bacterium selected, the biochemical reactor of the present invention may be used to cultivate microorganisms for methane fermentation or to proliferate microorganism for purification of groundwater or wastewater. It may also be used to reduce the level of ammonia nitrogen or BOD, using nitrifying bacteria or microorganisms and protozoa living in activated sludge.

Therefore, the raw liquid (96) may be a liquid medium for proliferation of microorganisms; it may also be groundwater or wastewater. The biochemical reactor will vary in scale depending on its application, ranging from laboratory use to factory use, especially large-scale municipal purification plants.

The vessel (4) is a cylindrical container having a bottom. The vessel (4) shown in the figure has an open top, but it may be closed with a lid (not shown). In general, an open vessel is used for aerobic bacteria and a closed vessel is used for anaerobic bacteria. The cylindrical vessel may be replaced by a box-like container.

The transport tube (1) comprises a funnel-shaped carrier collector (7), a straight fluid guide (3) having a suction inlet (3h) at its top, and a centrifugal force generator (2) which is curved sideward. The transport tube (1) has a rotating shaft (8) along its axis. An optional carrier collector (7) may be provided to more effectively collect the carrier. The shaft (8) has a lower end fixed to the inner wall of the curved tube of the centrifugal force generator (2). Also, the shaft (8) has an upper end connected to a rotary drive (9), for example an electric motor, through reduction gears or over-drive gears. Therefore, the rotary force of the rotary drive (9) is transmitted to the transport tube (1) through the shaft (8).

Figure 3:
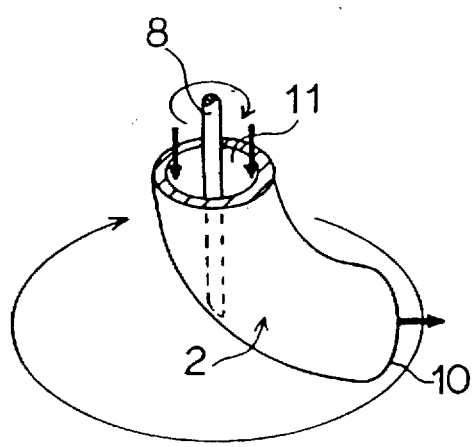
FIG. 3 is a schematic drawing showing the structure of the centrifugal force generator.

The centrifugal force generator (2) is a tubular member extending outward from the axis of rotation of the rotary drive (9), as shown in FIG. 3. The tubular member terminates in an outlet (10) and extends upward, forming a suction passage (11) around the axis of rotation of the centrifugal force generator (2). When the centrifugal force generator (2) turns, the fluid is moved from the suction passage (11) to the outlet (10) by centrifugal force. Although not required, it is preferred that the suction passage (11) is in alignment with the axis of rotation, because non-alignment reduces the distance between the suction passage (11) and the outlet (10), thereby reducing the centrifugal force generated.

Figure 4:
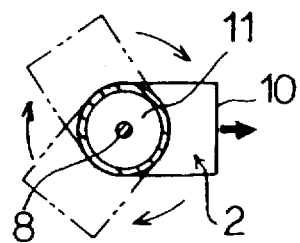
FIG. 4 is a diagram showing how the centrifugal force generator rotates.

As the transport tube (1) turns about the shaft (8), centrifugal force is exerted on the fluid in the centrifugal force generator (2), thereby causing the fluid to be discharged through the outlet (10) and the fresh fluid to enter through the suction passage (11). Since the outlet (10) turns through 360° as shown in FIG. 4, the transport of the fluid (or the discharge of the fluid from the outlet (10)) also stirs the fluid in the vessel. The stirring brings the fluid into intimate contact with the carrier, promoting the biodegradation process and homogenizing the raw liquid in the vessel.

The fluid passes through the transport tube and leaves the outlet (10). The transport tube permits a large amount of fluid to flow slowly without damaging the carrier (95). Therefore, the carrier (95) can be used continuously for a long period of time. The rotary drive (9) needs only a small amount of power to rotate the transport tube (1). In addition, the rotary drive has a simple structure, is virtually trouble-free and inexpensive to produce.

When used with an immobilizing carrier, the biochemical reactor of liquid current type of the present invention produces a marked effect in the treatment of raw liquid. The subject invention may also be used without an immobilizing carrier, for instance, for treating a raw liquid having microorganisms suspended directly therein. As described above, the raw liquid may then be transported in large quantities using a low-power rotary drive.

The following further describes modifications of the embodiments. The centrifugal force generator (2) may be sharply bent at the end as shown in FIG. 5(a); inclined straight as shown in FIG. 5(b); or pronged as shown in FIG. 6. A pronged outlet may have, as illustrated, two outlets (10), (10) or it may have three or more outlets (10) (not shown).

Figure 7:
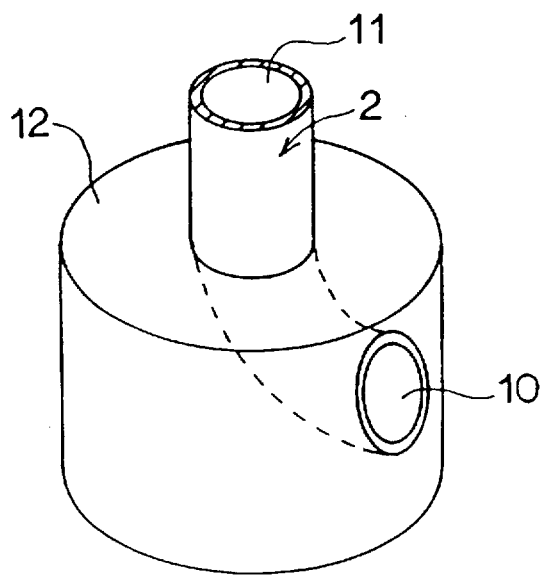
FIG. 7 is a schematic drawing showing another type of the centrifugal force generator.
Figure 8:
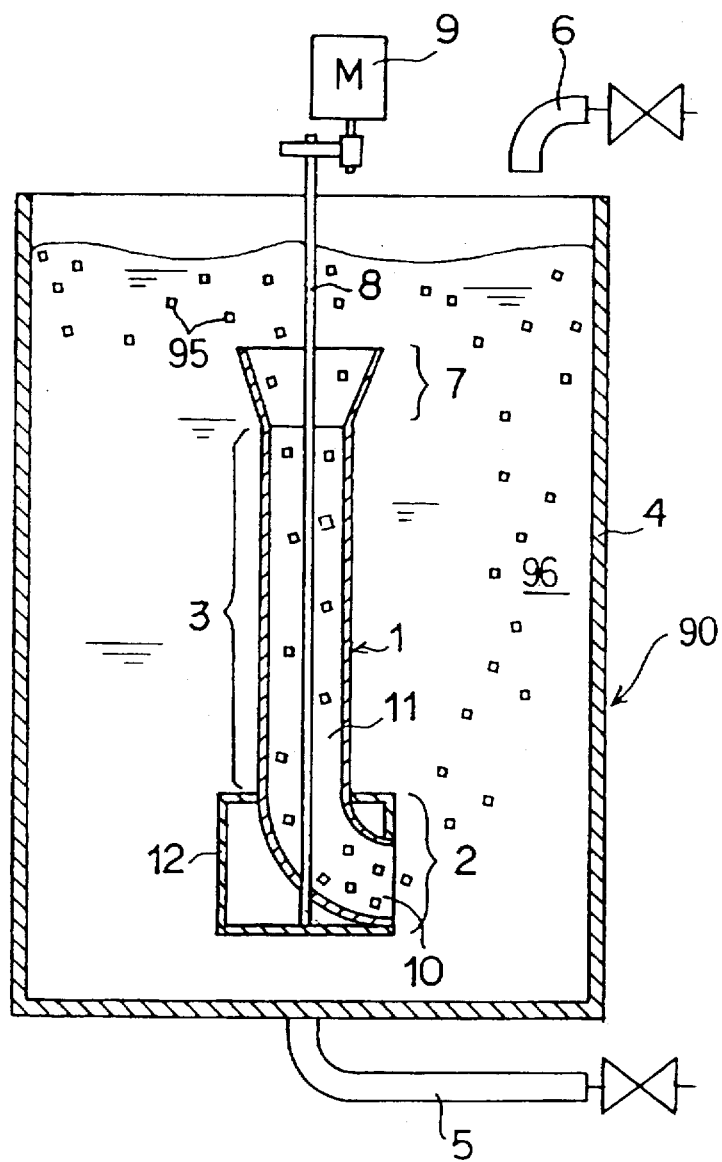
FIG. 8 is a sectional view of one example of the biochemical reactor of liquid current type which employs the centrifugal force generator shown in FIG. 7.

The centrifugal force generator (2) may be modified as shown in FIGS. 7 and 8 to further reduce liquid resistance during rotation. The centrifugal force generator (2) is enclosed by a hollow cylindrical casing (12) of approximately the same radius as the maximum radius of rotation of the centrifugal force generator (2). The casing (12) also has a circumferential wall having an opening communicating with the outlet (10) of the centrifugal force generator (2). Because the hollow cylindrical casing (12) has a symmetry of rotation, as it rotates with the centrifugal force generator (2), very little resistance is generated during its rotation because it has a symmetry of rotation. Consequently, only a small amount of power is needed to power the rotary drive (9).

Figure 9:
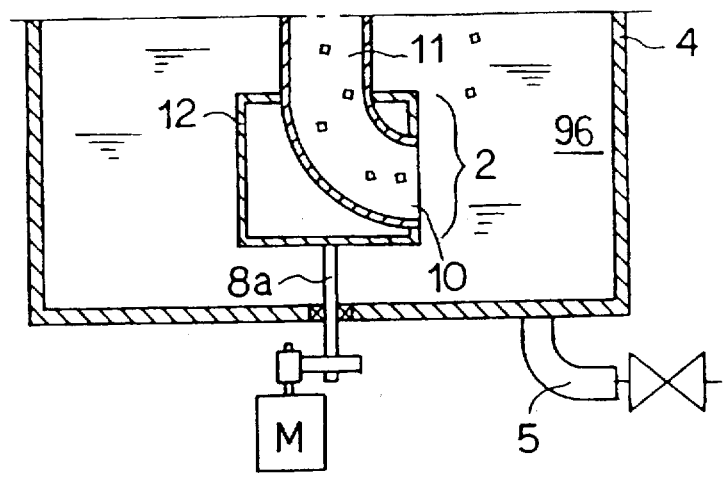
FIG. 9 is a sectional view showing a modified embodiment in which the centrifugal force generator is provided with a rotary drive.

Another modification is shown in FIG. 9. In this embodiment, the rotary drive (9) is under the centrifugal force generator (2). A shaft (8a) for rotating the centrifugal force generator penetrates the bottom of the vessel (4) and is fixed to the bottom of the hollow cylindrical casing (12). Because the shaft does not pass through the inside of the transport tube, the carrier flows more smoothly through the transport tube (1).

Figure 10:
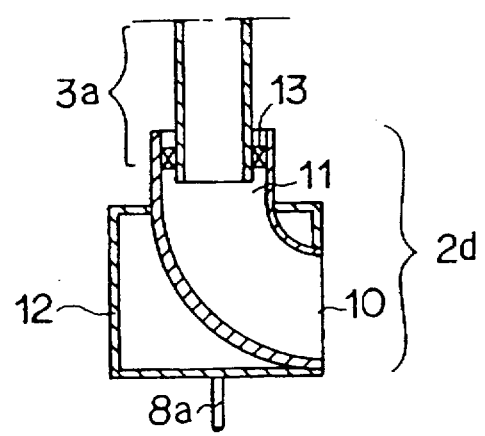
FIG. 10 is a sectional view showing a modified embodiment in which the centrifugal force generator is capable of rotating with respect to the fluid guide.

Another modification is shown in FIG. 10. Unlike the foregoing embodiments, in this embodiment the fluid guide (3a) remains stationary while the centrifugal force generator (2d) rotates. The centrifugal force generator (2d) and the fluid guide (3a) are joined through a bearing (13) so that the former rotates independently of the latter. In this modification, the rotary drive (9) requires only a small amount of power to rotate the centrifugal force generator.

Figure 11:
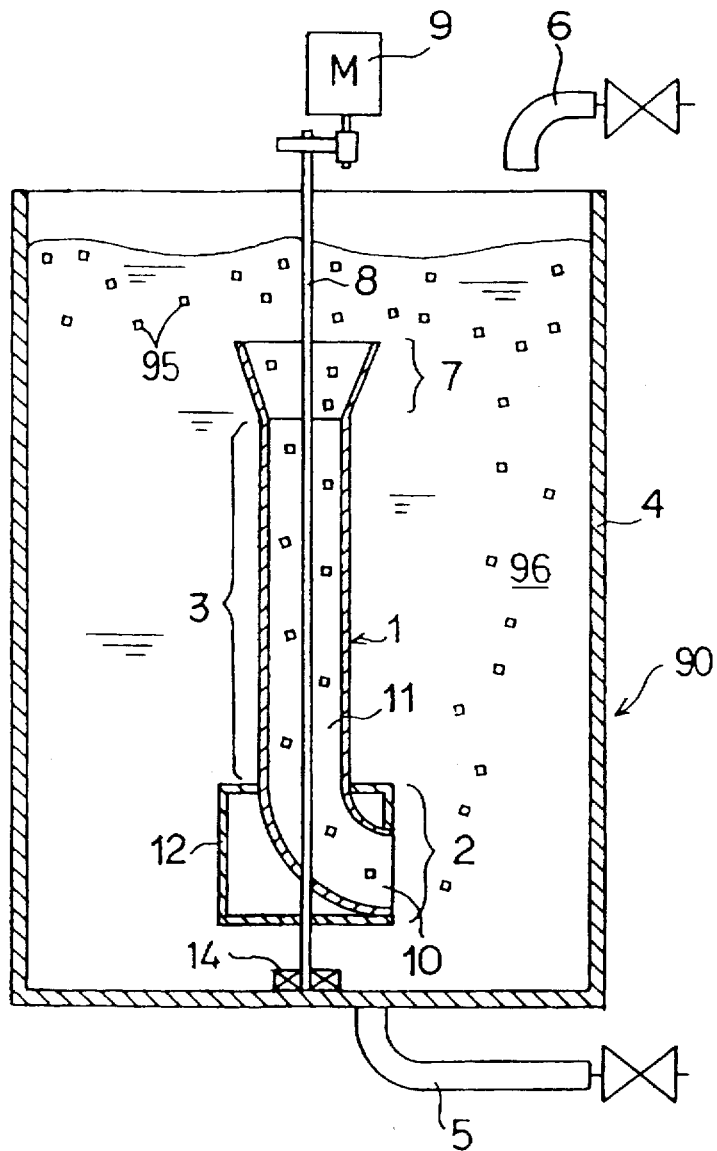
FIG. 11 is a sectional view of an embodiment in which the transporting pipe is held at its upper and lower parts so that it will not vibrate laterally.
Figure 12:
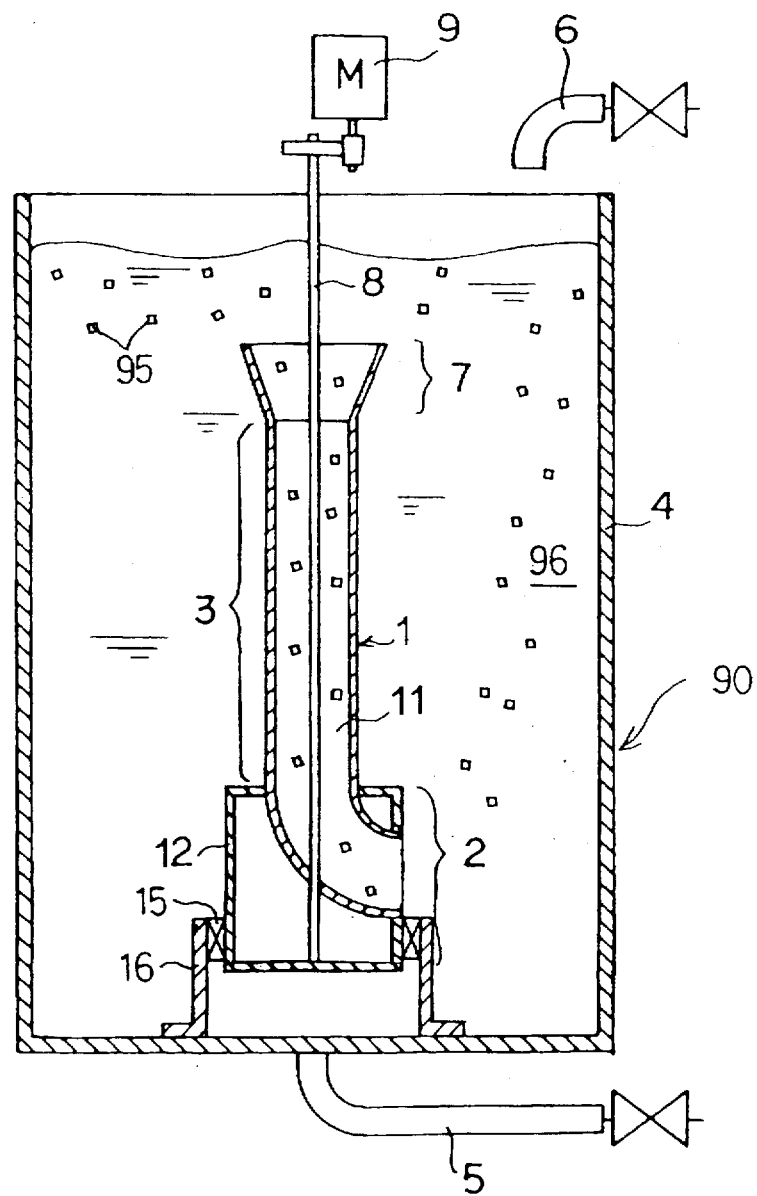
FIG. 12 is a sectional view of an embodiment in which the transporting pipe is held at its upper and lower parts so that it will not vibrate laterally.

The modification shown in FIGS. 11 and 12 prevents the transport tube (1) from vibrating laterally at its lower end. In the modification shown in FIG. 1, the shaft (8) extends to the bottom of the vessel and its end is rotatably held at the bottom of the vessel by a bearing (14). In the modification shown in FIG. 12, the hollow cylindrical casing (12) is encased by a supporting cylinder (16), with a bearing (15) between them. In either modification, the upper and lower parts firmly held in position and lateral vibration of the the transport tube (1) during its rotation is minimized.

Figure 13:
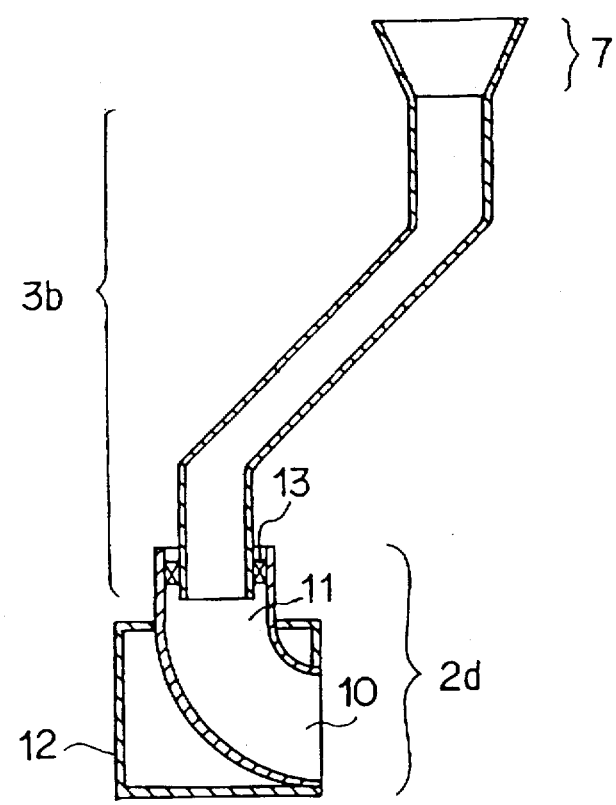
FIG. 13 is a sectional view showing a modified embodiment in which the fluid guide is bent.

The embodiment shown in FIG. 12 may be further modified as shown in FIG. 13. In this embodiment, the stationary fluid guide (3b) may be bent because it does not rotate with the centrifugal force generator (2d). This modification is useful when objects in the vessel would hinder a straight fluid guide. In another modification shown in FIG. 14 a portion of the transport tube (1') runs outside the vessel.

Figure 15:
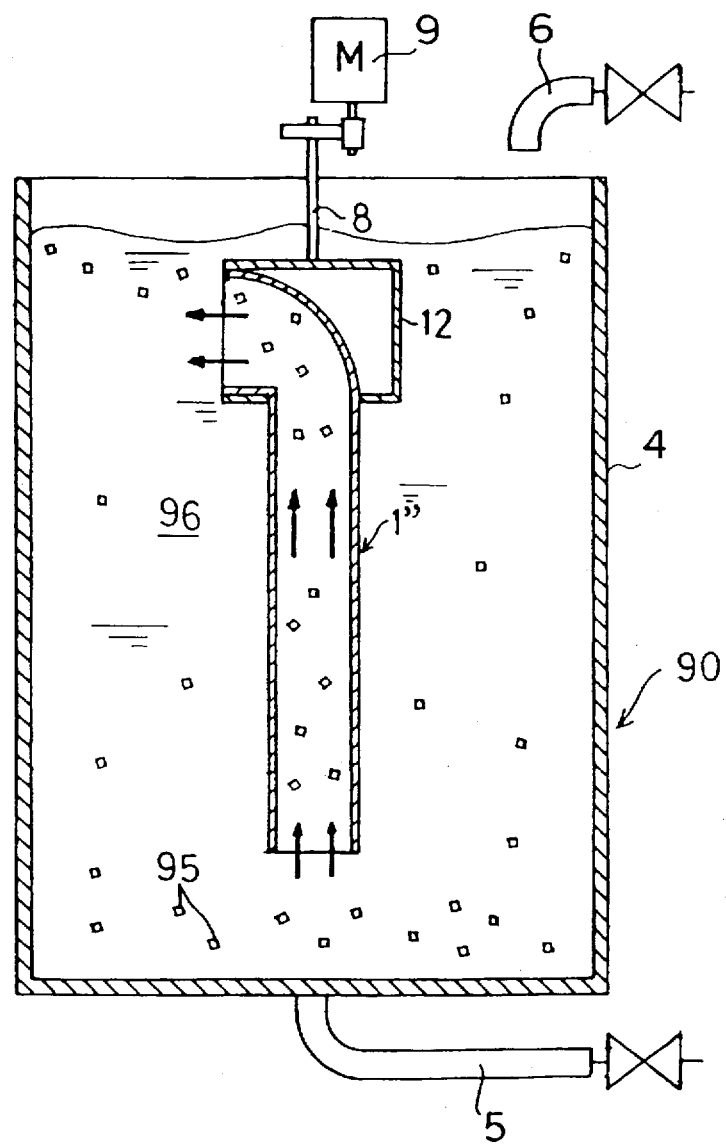
FIG. 15 is a sectional view showing an embodiment in which the fluid is transported upward in the vessel.

In all the foregoing embodiments, the fluid is transported in a downward direction, from the upper part of the vessel to the lower part of the vessel. According to the present invention, it is also possible to design the system so that the fluid is transported in the opposite direction. As shown in FIG. 15, the centrifugal force generator may be installed at the upper part of the transport tube (1") and thus draw the fluid from bottom of the vessel. This embodiment is useful in handling a carrier which tends to precipitate because its specific gravity is higher than that of the raw liquid.

Figure 16:
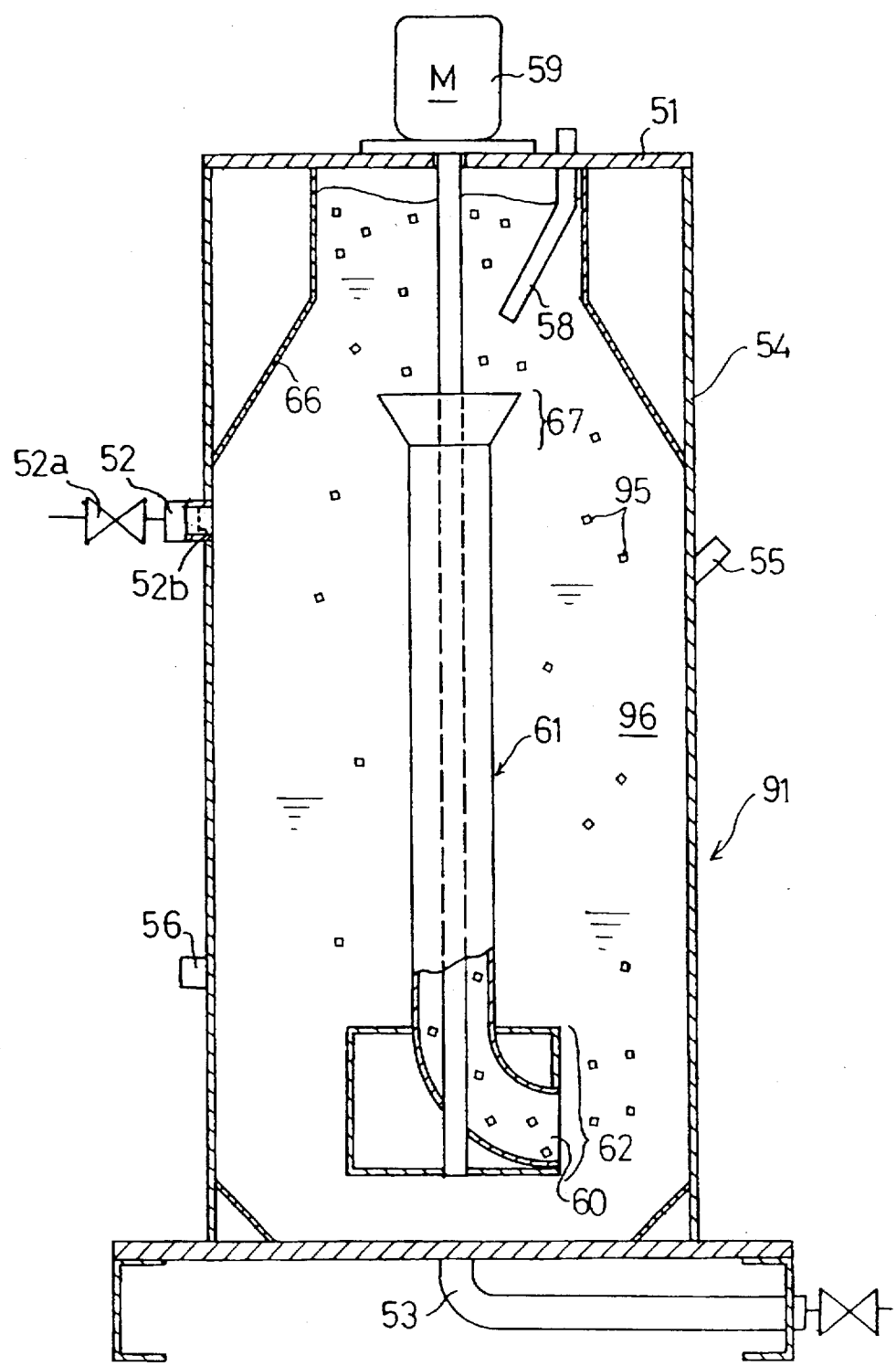
FIG. 16 is a sectional view showing an embodiment of the biochemical reactor of liquid current type according to the present invention.

The following is a description of further embodiments of the present invention. FIG. 16 shows a system designed to treat a liquid containing an immobilizing carrier whose specific gravity is less than that of the raw liquid.

The vessel (54) is an airtight cylindrical container having a bottom and a lid. For cultivation of anaerobic bacteria such as denitrifying bacteria, it is important to keep air out. The upper lid (51) may be opened and closed to allow the immobilizing carrier to be replenished and the vessel to be cleaned. The lid is made of an air-tight material. An air-tight lid is not necessary when the vessel is used to cultivate aerobic bacteria. For anaerobic bacteria, the vessel is filled with nitrogen, whereas for aerobic bacteria, the vessel is supplied with oxygen. Nitrogen or oxygen may be introduced into the vessel using a conventional diffuser tube or sparger.

The equipment described in the preceding paragraphs uses, for example, a porous, floating carrier (95). The following describes equipment used for the denitrification of groundwater.

Groundwater is fed into the vessel (54) having a lid (51) through a supply tube (58). A discharge tube (52) located on the side wall of the vessel (54) discharges the treated liquid from the vessel (54). A drain (53) at the bottom of the vessel occasionally discharges residual precipitates from the vessel. A filter (52b) and a valve (52a) are located in the middle of the discharge tube (52). When denitrification reaches a prescribed level, the treated liquid is discharged by opening the valve (52a). The valve (52a) may be manually operated, or, alternatively, it may be automatically operated by a mechanism connected to a sensor which detects nitrogen concentration. The sensor may be inserted into the vessel through a port (55). The liquid in the vessel may be heated by a heater inserted into the vessel through a port (56).

As shown in FIG. 8, a transport tube (61) located along the vertical axis of the vessel is provided with a funnel-shaped carrier collector (67) positioned below the level of the raw liquid (96). The transport tube (61) draws the carrier (95) through the funnel-shaped carrier collector (67), down through the tube, and then returns the carrier (95) to the vessel from the outlet (60) of the centrifugal force generator (62).

An upwardly tapered wall (66) surrounds the carrier collector (67) at the upper part of the vessel. The tapered wall (66) helps gather the floating carrier (95) around the carrier collector (67). The carrier collector (67) may be positioned at the center of the vessel, as shown in FIG. 8, or at any other position where the carrier accumulates in the vessel. For example, although illustrated with a uniform angle, the carrier collector (67) may be displaced from the center if the slope angle of the tapered wall (66) is varied from place to place along the periphery of the vessel.

Moreover, although illustrated as encircling the entire periphery, the tapered wall may extend for only a portion of periphery. Thus, there are many configurations of a tapered wall which help the carrier collector (67) collect the carrier. For example, the wall surrounding the carrier collector (67) may be partly inclined and partly vertical.

The optional funnel-shaped carrier collector may be a straight cylinder or, preferably, have a funnel-shaped opening. The tapered or inclined wall (66) may also be perforated to admit only the raw liquid. The raw liquid running through the perforated wall is discharged through a pipe fixed to the upper part of the vessel wall at the same height as the tapered wall (66).

The biochemical reactor of liquid current type constructed as described in the foregoing may be operated in the following manner.

The vessel (54) is filled with the carrier (95) and then charged with the raw liquid (96) through the supply tube (58). The treated liquid is discharged through the discharge tube (52) extending from the side wall of the vessel.

The reactor may be used in either batch or continuous modes. In batch mode, the carrier (95) and the raw liquid (96) are circulated in the reactor at predetermined times until the nitrogen concentration in the raw liquid falls below a standard. Then, the treated liquid is discharged and fresh raw liquid is charged. In continuous mode, the raw liquid is replenished at the same rate that the treated liquid is discharged.

The floating carrier (95) is collected in the vicinity of the carrier collector (67) by the annular tapered wall (66). The transport tube (61) moves the carrier (95) downward and the outlet (60) returns the carrier to the vessel. The carrier (95) rises through the vessel, and the preceding steps are repeated. During circulation of the carrier (95), nitrogen in the raw liquid is removed by microorganisms supported on the carrier (95).

Even if the carrier (95) has an apparent specific density lower than 1 (due to gas evolution) and therefore accumulates near the surface of the liquid, the reactor described above is able to recover the carrier through the funnel-shaped carrier collection (67). The carrier collector (67) is positioned at the center of the vessel as viewed from above, and the carrier (95) moves toward that position. Therefore, the carrier (95) is uniformly distributed and circulated throughout the vessel.

The vigorous flow and agitation of the carrier (95) permits the carrier (95) to be in in high concentrations in the liquid, thereby increasing the efficiency of treatment. In the biochemical reactor of the present invention, the volume of the carrier accounts for about 60% of the capacity of the vessel, compared to about 50% in the conventional biochemical reactor shown in FIG. 24. It should be noted that the carrier (95) floats whenever its specific gravity is lower than that of the raw liquid (96). As described above, floating occurs when the specific gravity of the carrier decreases below 1. In addition, whether or not the carrier (95) floats depends on the flow of the raw liquid (96). Therefore, if there is an upward current, the carrier (95) will float even if its specific gravity is greater than that of the raw liquid.

Figure 17:
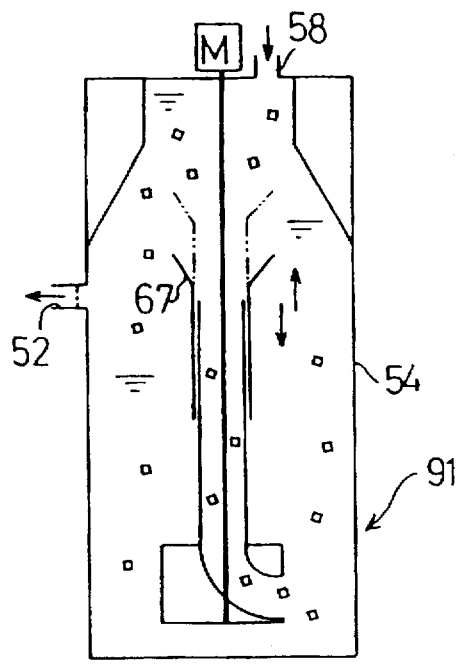
FIG. 17 is a sectional view showing an embodiment in which the carrier inlet is movable vertically.

FIG. 17 shows an embodiment wherein the carrier collector (67) may be moved up and down. The advantage of a movable carrier collector is that it can be lowered to a proper position if it is difficult to efficiently recover densely accumulated carrier near the surface of the raw liquid.

Figure 18:
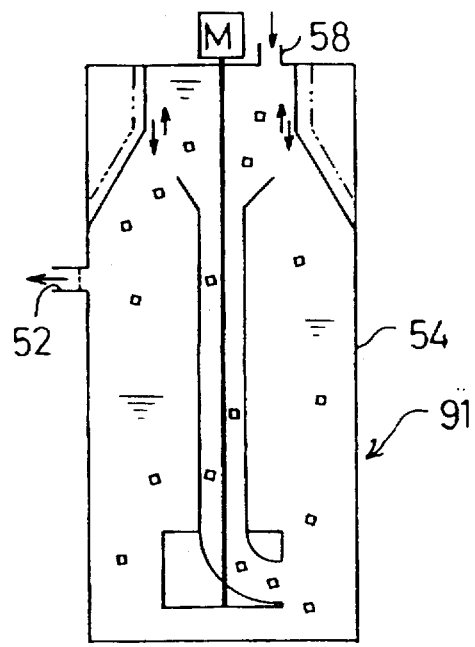
FIG. 18 is a sectional view showing an embodiment in which the annular inclined wall is movable vertically.
Figure 19:
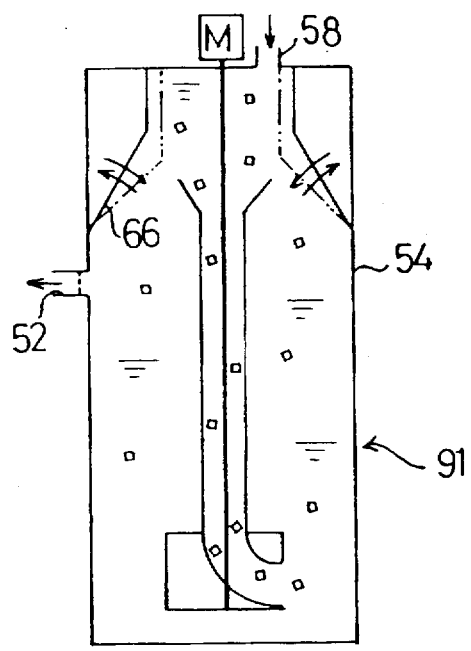
FIG. 19 is a sectional view showing an embodiment in which the annular inclined wall is capable of adjustment of the slope angle.

An upward and downwardly movable annular tapered wall (66) is depicted in FIG. 18. FIG. 19 depicts an embodiment wherein the slope angle of the tapered wall (66) is adjustable. Like the movable carrier collector (67), the movable or adjustable tapered wall (66) allows for more efficient collection of carrier accumulated near the surface of the liquid.

Figure 20:
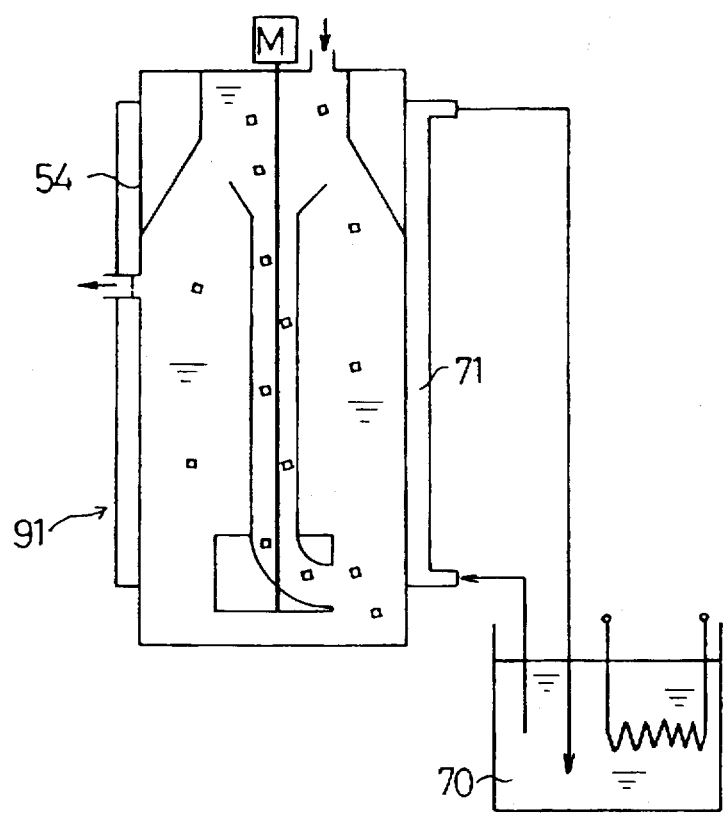
FIG. 20 is a sectional view showing an embodiment in which the vessel is provided with an outer jacket for warm water.

In the embodiment shown in FIG. 20, the vessel (54) is enclosed in an outer jacket (71) through which warm water (70) is circulated in order to promote the proliferation of microorganisms. Optimally the temperature for denitrifying bacteria has a maximum of 40° C. At temperatures above this limit, growth rate decreases. Alternatively, the vessel (54) may be heated by arranging heaters directly around the vessel (54) or by inserting a heater into the raw liquid through a port formed in the side wall of the vessel as described above.

In addition to the cylindrical vessel described in the foregoing embodiments, the vessel may also be cubic in shape.

Figure 21:
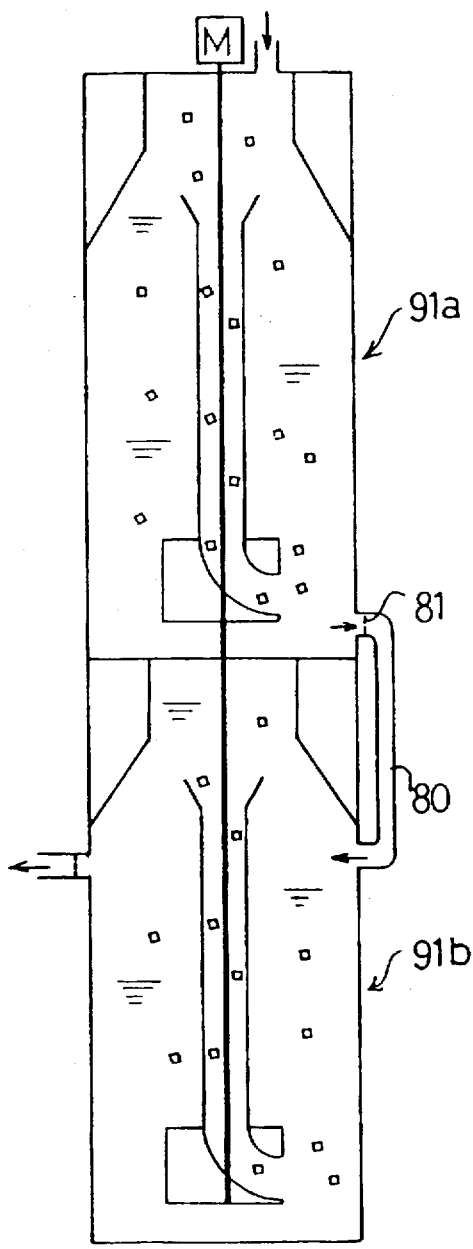
FIG. 21 is a sectional view showing an embodiment in which two units of the biochemical reactor of liquid current type are vertically arranged in tandem.

The above-described embodiments may be used alone and, also, may be used in tandem. As shown in FIG. 21, two units of biochemical reactors (91a)(91b) are placed on top of each other and are connected through a connecting pipe (80). In this embodiment, the raw liquid is treated twice, once in the upper unit and once in the lower unit. The connecting pipe (80) is provided with a filter (81) which is impermeable to the carrier but permeable to raw liquid. The number of biochemical reactors of the subject invention which may be joined in series is not limited to two.

The reactors of the present invention may also be used in a side by side arrangment of two or more units. Multi-stage treatment reduces the amount of circulation of raw liquid required in each vessel, leading to more efficient treatment.

A purification system for groundwater or wastewater may be constructed by incorporating the biochemical reactor of the present invention into existing water purification facilities made up of sedimentation basins, filter tanks, and chemical treatment tanks, and the like. It may be placed before or after the existing purification facility. If the purification facility is made up of several units, the reactor of the present invention may be placed at any point among them.

In addition to incorporating the biochemical reactors into an existing purification system, the transport mean of present invention may also be used in a general-purpose fluid transport-stirring apparatus.

Figure 22:
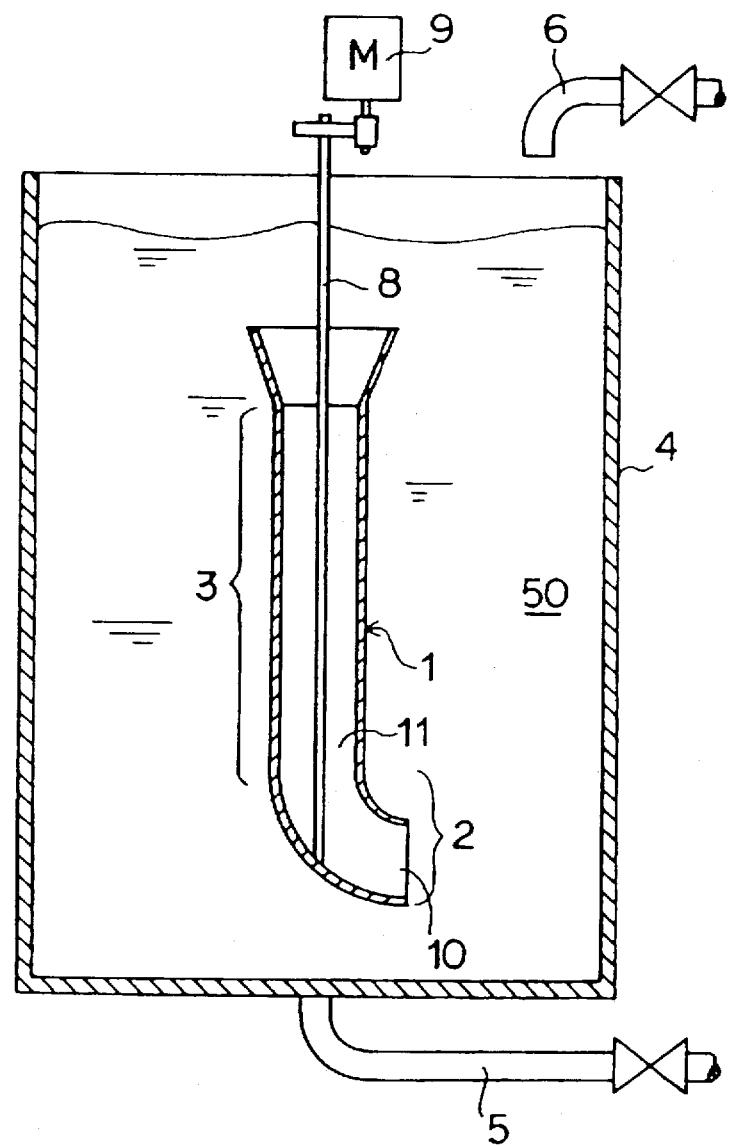
FIG. 22 is a sectional view showing an embodiment of the fluid transport-stirring unit according to the present invention.

FIG. 22 is a vertical sectional view showing an embodiment of the general-purpose fluid transport-stirring apparatus. Although similar in structure to the biochemical reactor shown in FIG. 1, the liquid in the vessel (4) of this apparatus does not contain a carrier.

The fluid transport-stirring apparatus is capable of simultaneously transporting the liquid (50) downward and stirring the liquid (50) in the vessel (4). Consequently, this apparatus is useful in transporting and/or stirring a liquid.

The fluid (50) passes through the transport tube (1) and exits through the outlet (10). The transport tube is able to transport and stir large amounts of fluid because no objects except the shaft disrupt the smooth flow of the fluid within the transport tube. The rotary drive means (9) requires only a small amount of power to rotate the transport tube (1). In addition, the subject invention has a simple structure, is virtually trouble-free and inexpensive to produce.

The fluid transport-stirring apparatus of the present invention can be used to transport any fluid, including, for example, a gas, a liquid, or a slurry containing a large number of small solids. When transporting a slurry, the present invention also protects the solids from damage.

Figure 23:
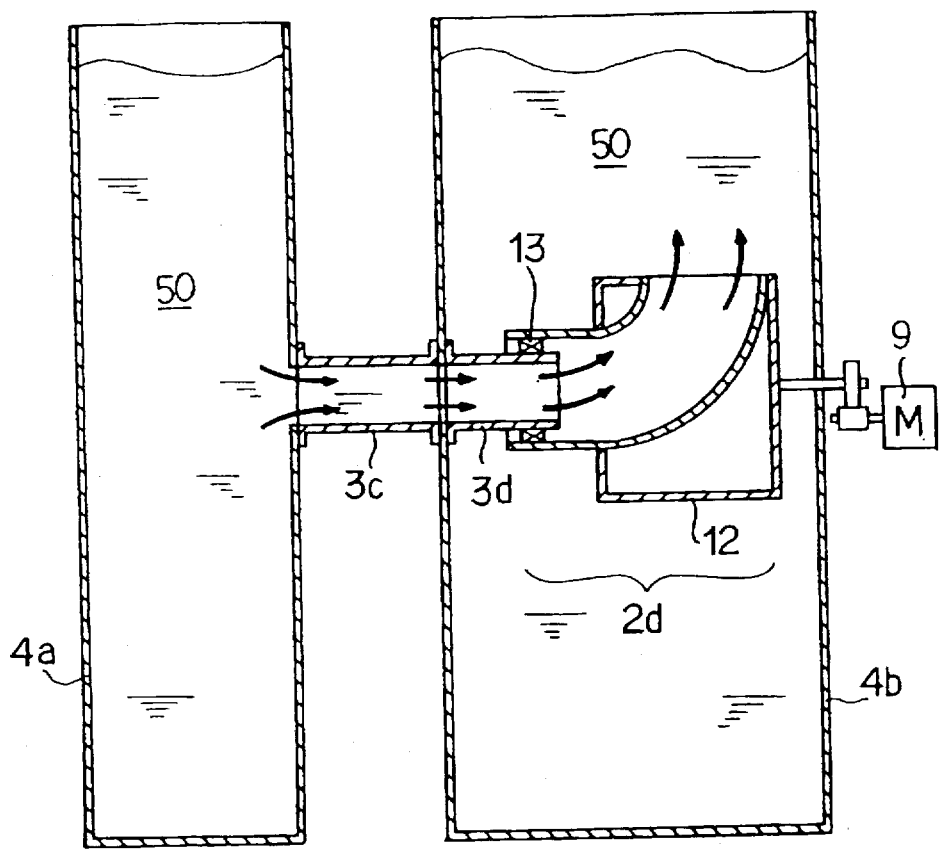
FIG. 23 is a sectional view showing an embodiment designed to transport a fluid from one vessel to another.

This apparatus can also be used to transport a liquid from one vessel to another. As shown in FIG. 23, two vessels (4a) (4b) are connected by a fluid guide (3c). An auxiliary fluid guide (3d) extends fluid guide (3c) into the second vessel (4b). The auxiliary fluid guide (3d) is connected, through a bearing (13), to a centrifugal generator (2d) which is enclosed by a hollow cylindrical casing (12). The centrifugal generator (2d) and the hollow cylindrical casing (12) are turned by a horizontal shaft. The hollow cylindrical casing (12) reduces the resistance generated upon rotation of the centrifugal force generator (2) in the liquid.

The following example is provided to illustrate the claimed invention and should not be construed as limiting the invention in any way.

EXAMPLE

Denitrification

A reactor, as shown in FIG. 16, having the following specifications was used to determine denitrification efficiency. The vessel (54) had a capacity of 0.5 m$^3$, the transport tube (61) measured 1180 mm (including the carrier collector (67) and the centrifugal force generator (62) in length and had an inside diameter of 110 mm. The centrifugal force generator (62) turned at a rate of 150 rpm.

Figure 25:
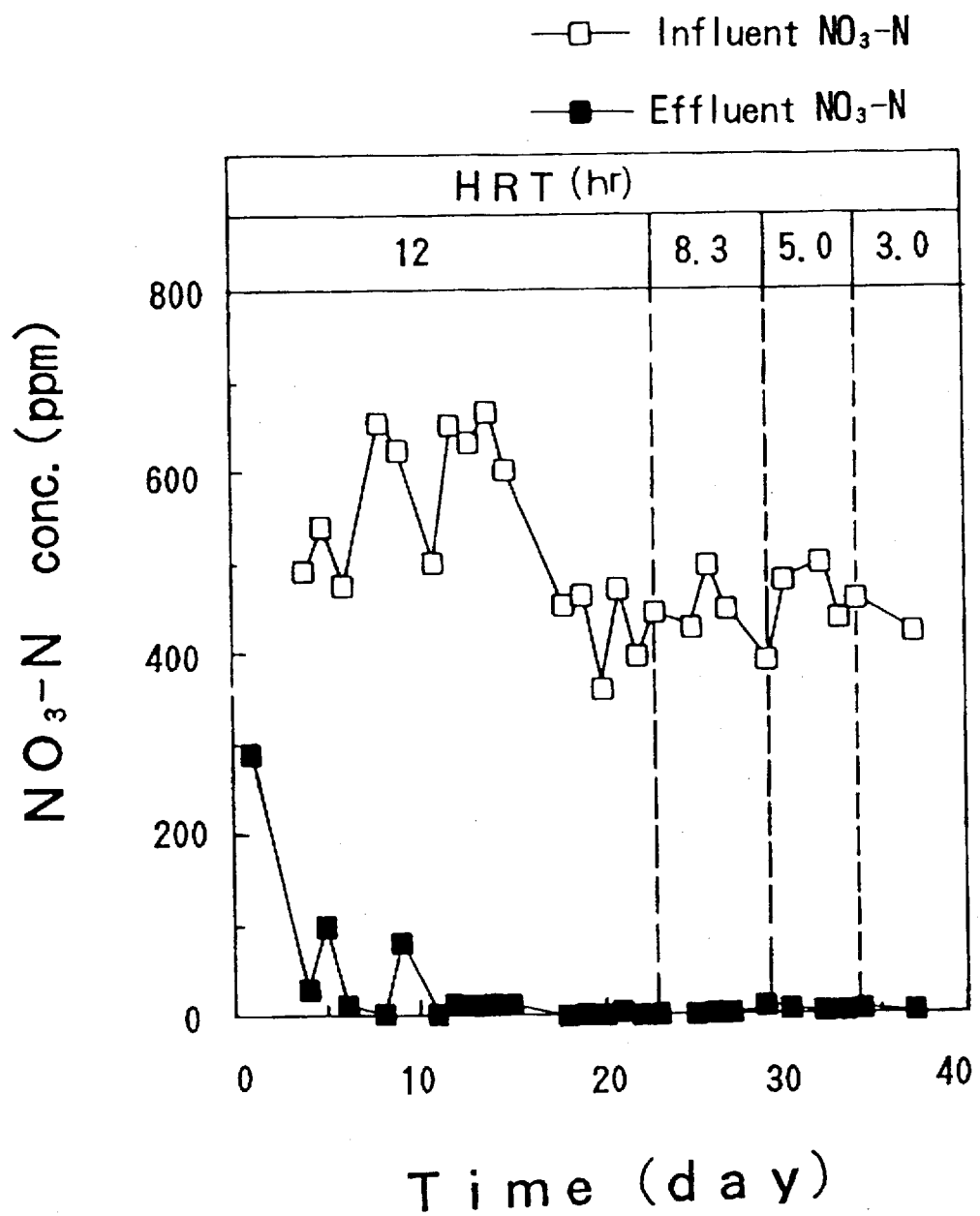
FIG. 25 is a graph showing the results of experiment on denitrification by the biochemical reactor of liquid current type according to the present invention.
Figure 26:
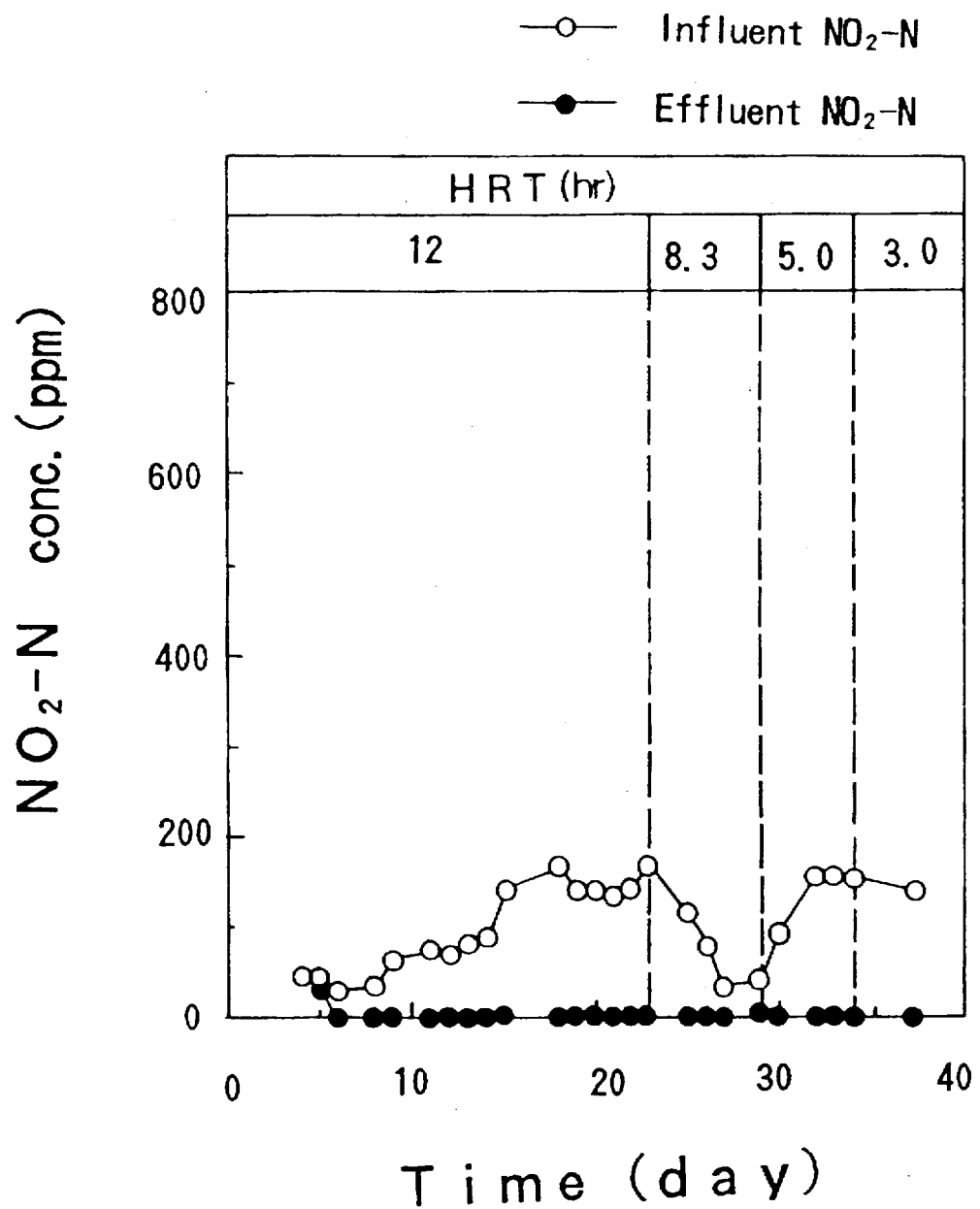
FIG. 26 is a graph showing the results of experiment on denitrification by the biochemical reactor of liquid current type according to the present invention.

The biochemical reactor was charged with industrial wastewater. The concentrations of nitrate nitrogen ($NO_3$—N) and nitrite nitrogen ($NO_2$—N) in the industrial wastewater were monitored under anaerobic conditions. Denitrification was carried out by using denitrifying bacteria obtained from common activated sludge. The denitrifying bacteria were immobilized on a carrier comprised of an open-cell cellulose foam having a particle diameter of 3 mm. The carrier (0.2 m$^3$) was charged into the vessel (54). The ratio of charging was about 20% in terms of apparent specific gravity and about 40% in terms of volume. The wastewater remained in the vessel for 12 h, 8.3 h, 5.0 h, or 3.0 h. Results are shown in FIGS. 25 and 26. Note that the concentrations of both $NO_3$—N and $NO_2$—N in the effluent (treated liquid) are lower than those in the influent (raw liquid). Also note that the reactor maintained denitrifying ability even when the wastewater remained in the vessel for only 3.0 hours. Thus, the reactor is capable of denitrifying a large amount of industrial wastewater in a short time.

We claim:

1. A liquid current biochemical reactor for proliferating microorganisms or selectively removing or converting a component in a raw liquid by biodegradation, said biochemical reactor comprising:

a vessel to hold an immobilizing carrier and a raw liquid;

a transport assembly for moving said immobilizing carrier and said raw liquid from one place to another in said vessel, wherein said transport assembly comprises:

a.) a rotary drive;

b.) a tubular centrifugal force generator which is rotated by said rotary drive about an axis of rotation and said centrifugal force generator having a suction passage extending outward from the axis of rotation and terminating with an outlet; and c.) a tubular fluid guide having an inlet and an internal passage extending from said inlet and communicating with said suction passage of said centrifugal force generator, said inlet of said fluid guide and said outlet of said centrifugal force generator being positioned apart in said vessel.

2. The reactor of claim 1, wherein the inlet of the fluid guide and the outlet of the centrifugal force generator are spaced apart vertically within the vessel.

3. The reactor of claim 2, wherein the vessel has an upper portion, said upper portion being tapered to form a narrowed region and wherein the inlet of the fluid guide is positioned within said narrowed region to collect said immobilizing carrier.

4. The reactor of claim 3, wherein the inlet of the fluid guide is movable and adjustable within said narrowed region.

5. The reactor of claim 1, wherein the fluid guide includes a straight member having an axis, said straight member adapted to introduce the raw fluid to the suction passage of the centrifugal force generator and wherein the axis of the straight member is aligned with the axis of rotation of the tubular force generator.

6. The reactor of claim 2, wherein the fluid guide includes a straight member having an axis, said straight member adapted to introduce the raw fluid to the suction passage of the centrifugal force generator and wherein the axis of the straight member is aligned with the axis of rotation of the tubular force generator.

7. The reactor of claim 3, wherein the fluid guide includes a straight member having an axis, said straight member adapted to introduce the raw fluid to the suction passage of the centrifugal force generator and wherein the axis of the straight member is aligned with the axis of rotation of the tubular force generator.

8. The reactor of claim 4, wherein the fluid guide includes a straight member having an axis, said straight member adapted to introduce the raw fluid to the suction passage of the centrifugal force generator and wherein the axis of the straight member is aligned with the axis of rotation of the tubular force generator.

9. The reactor of claim 1, wherein the centrifugal force generator and the fluid guide comprise a single rotatable tube.

10. The reactor of claim 3, wherein the centrifugal force generator and the fluid guide comprise a single rotatable tube.

11. The reactor of claim 1, wherein the fluid guide is stationary with respect to the centrifugal force generator.

12. The reactor of claim 3, wherein the fluid guide is stationary with respect to the centrifugal force generator.

13. The reactor of claim 1, wherein the centrifugal force generator has a maximum radius of rotation and wherein said centrifugal force generator is enclosed by a hollow cylindrical casing having a circumferential wall, which hollow cylindrical casing has approximately the same radius as the maximum radius of rotation of the centrifugal force generator and further has an opening in its circumferential wall in fluid communication with the outlet of the centrifugal force generator.

14. The reactor of claim 9, wherein the centrifugal force generator has a maximum radius of rotation and wherein said centrifugal force generator is enclosed by a hollow cylindrical casing having a circumferential wall, which hollow cylindrical casing has approximately the same radius as the maximum radius of rotation of the centrifugal force generator and further has an opening in its circumferential wall in fluid communication with the outlet of the centrifugal force generator.

15. The reactor of claim 11, wherein the centrifugal force generator has a maximum radius of rotation and wherein said centrifugal force generator is enclosed by a hollow cylindrical casing having a circumferential wall, which hollow cylindrical casing has approximately the same radius as the maximum radius of rotation of the centrifugal force generator and further has an opening in its circumferential wall in fluid communication with the outlet of the centrifugal force generator.

16. The reactor of claim 12, wherein the centrifugal force generator has a maximum radius of rotation and wherein said centrifugal force generator is enclosed by a hollow cylindrical casing having a circumferential wall, which hollow cylindrical casing has approximately the same radius as the maximum radius of rotation of the centrifugal force generator and further has an opening in its circumferential wall in fluid communication with the outlet of the centrifugal force generator.

17. The reactor of claim 1, further comprising a feed element for feeding a raw liquid to the vessel continuously and a discharge element for discharging a treated liquid from the vessel continuously.

18. The reactor of claim 9, further comprising a feed element for feeding a raw liquid to the vessel continuously and a discharge element for discharging a treated liquid from the vessel continuously.

19. The reactor of claim 11, further comprising a feed element for feeding a raw liquid to the vessel continuously and a discharge element for discharging a treated liquid from the vessel continuously.

20. The reactor of claim 1 wherein said reactor is a first reactor having a feed element for introduction of raw liquid into said first reactor and a discharge element for withdrawal of treated raw fluid from said first reactor and further comprising a second biochemical reactor also having a feed element for introduction of liquid into said second reactor and a discharge element for withdrawal of treated fluid from said second reactor and wherein the first reactor discharge element is in fluid communication with the feed element of said second reactor.

21. The reactor of claim 3 wherein said reactor is a first reactor having a feed element for introduction of raw liquid into said first reactor and a discharge element for withdrawal of treated raw fluid from said first reactor and further comprising a second biochemical reactor also having a feed element for introduction of liquid into said second reactor and a discharge element for withdrawal of treated fluid from said second reactor and wherein the first reactor discharge element is in fluid communication with the feed element of said second reactor.

22. The reactor of claim 9 wherein said reactor is a first reactor having a feed element for introduction of raw liquid into said first reactor and a discharge element for withdrawal of treated raw fluid from said first reactor and further comprising a second biochemical reactor also having a feed element for introduction of liquid into said second reactor and a discharge element for withdrawal of treated fluid from said second reactor and wherein the first reactor discharge element is in fluid communication with the feed element of said second reactor.

23. The reactor of claim 11 wherein said reactor is a first reactor having a feed element for introduction of raw liquid into said first reactor and a discharge element for withdrawal of treated raw fluid from said first reactor and further comprising a second biochemical reactor also having a feed element for introduction of liquid into said second reactor and a discharge element for withdrawal of treated fluid from said second reactor and wherein the first reactor discharge element is in fluid communication with the feed element of said second reactor.

24. The reactor of claim 3 further comprising an immobilizing carrier with an apparent specific gravity less than about 1.2.

25. The reactor of claim 9 further comprising an immobilizing carrier with an apparent specific gravity less than about 1.2.

26. The reactor of claim 11 further comprising an immobilizing carrier with an apparent specific gravity less than about 1.2.

27. The reactor of claim 1 further comprising an immobilizing carrier supporting denitrifying bacteria.

28. The reactor of claim 9 further comprising an immobilizing carrier supporting denitrifying bacteria.

29. The reactor of claim 11 further comprising an immobilizing carrier supporting denitrifying bacteria.

30. The reactor of claim 1 further comprising an immobilizing carrier supporting methane-generating bacteria.

31. The reactor of claim 9 further comprising an immobilizing carrier supporting methane-generating bacteria.

32. The reactor of claim 11 further comprising an immobilizing carrier supporting methane-generating bacteria.

33. The reactor of claim 1 further comprising an activated sludge layer containing an immobilizing carrier supporting nitrifying bacteria or microorganisms suitable for the reduction of ammonia nitrogen or BOD.

34. The reactor of claim 9 further comprising an activated sludge layer containing an immobilizing carrier supporting nitrifying bacteria or microorganisms suitable for the reduction of ammonia nitrogen or BOD.

35. The reactor of claim 11 further comprising an activated sludge layer containing an immobilizing carrier supporting nitrifying bacteria or microorganisms suitable for the reduction of ammonia nitrogen or BOD.

36. A fluid transport-stirring apparatus which comprises:
   a rotary drive; and
   a centrifugal force generator that is rotated by said rotary drive about an axis of rotation and which generator is positioned in a vessel suitable for holding a fluid, wherein said centrifugal force generator comprises:
   a.) a suction tube extending outwardly from the axis of rotation of said centrifugal force generator to a suction tube outlet; and
   b.) a suction passageway extending along the axis of rotation in fluid communication with the suction tube outlet.

37. The fluid transport-stirring apparatus of claim 36, wherein the centrifugal force generator further comprises a fluid guide for introducing fluid to the suction passageway and having an axis aligned with the axis of rotation of the centrifugal force generator.

38. The fluid transport-stirring apparatus of claim 37, wherein the centrifugal force generator and the fluid guide comprise a single rotatable tube.

39. The fluid transport-stirring apparatus of claim 37, wherein the fluid guide is stationary with respect to centrifugal force generator.

40. The fluid transport-stirring apparatus of claim 37, wherein the centrifugal force generator has a maximum radius of rotation and wherein said centrifugal force generator is enclosed by a hollow cylindrical casing having a circumferential wall, which hollow cylindrical casing has approximately the same radius as the maximum radius of rotation of the centrifugal force generator and further has an opening in its circumferential wall in fluid communication with the outlet of the centrifugal force generator.

41. The fluid transport-stirring apparatus of claim 38, wherein the centrifugal force generator has a maximum radius of rotation and wherein said centrifugal force generator is enclosed by a hollow cylindrical casing having a circumferential wall, which hollow cylindrical casing has approximately the same radius as the maximum radius of rotation of the centrifugal force generator and further has an opening in its circumferential wall in fluid communication with the outlet of the centrifugal force generator.

42. The fluid transport-stirring apparatus of claim 39, wherein the centrifugal force generator has a maximum radius of rotation and wherein said centrifugal force generator is enclosed by a hollow cylindrical casing having a circumferential wall, which hollow cylindrical casing has approximately the same radius as the maximum radius of rotation of the centrifugal force generator and further has an opening in its circumferential wall in fluid communication with the outlet of the centrifugal force generator.

* * * * *

UNITED STATES PATENT AND TRADEMARK OFFICE
CERTIFICATE OF CORRECTION

PATENT : 5,753,110
DATED : May 19, 1998
INVENTOR(S) : Matsumura et al

It is certified that error appears in the above-identified patent and that said Letters Patent is hereby corrected as shown below:

On the title page, after [22] Filed: May 31, 1996, insert the following:

--[30]  Foreign Application Priority Data

May 31, 1995   [JP]   Japan...........133150--.

On the title page, item [56], after the Foreign Patent Documents, add the following:

--            OTHER DOCUMENTS

Takahara, Y. (ed.), Biological Treatment of Water (1980), published by Chikyu-Sha, pp. 14, 168, 324 and 325.

Japanese Publication No. 63-251077, published October 18, 1988, corresponding to Japanese Application No. 62-084901, filed April 8, 1987, (Dialog English translation of Abstract included)

UNITED STATES PATENT AND TRADEMARK OFFICE
CERTIFICATE OF CORRECTION

PATENT : 5,753,110
DATED : May 19, 1998
INVENTOR(S) : Matsumura et al

It is certified that error appears in the above-identified patent and that said Letters Patent is hereby corrected as shown below:

Japanese Publication No. 07-124580, published May 16, 1995, corresponding to Japanese Application No. 05-183493, filed June 30, 1993. (Dialog English translation of Abstract included)

Japanese Publication No. 62-021638, published January 30, 1987, corresponding to Japanese Application No. 60-159036, filed July 18, 1985. (Dialog English translation of Abstract included)

Japanese Publication No. 04-091779, published March 25, 1992, corresponding Japanese Application No. 02-205001, filed August 3, 1990. (Dialog English translation of Abstract included)

UNITED STATES PATENT AND TRADEMARK OFFICE
CERTIFICATE OF CORRECTION

PATENT NO. : 5,753,110

DATED : May 19, 1998

INVENTOR(S) : Masatoshi Matsumura et al.

Page 3 of 6

It is certified that error appears in the above-identified patent and that said Letters Patent is hereby corrected as shown below:

In the Figures

On Figure 1, delete "Figure 1" and insert --Fig. 1--.

On Figure 2, delete "Figure 2" and insert --Fig. 2--.

On Figure 3, delete "Figure 3" and insert --Fig. 3--.

On Figure 4, delete "Figure 4" and insert --Fig. 4--.

Figure 5:
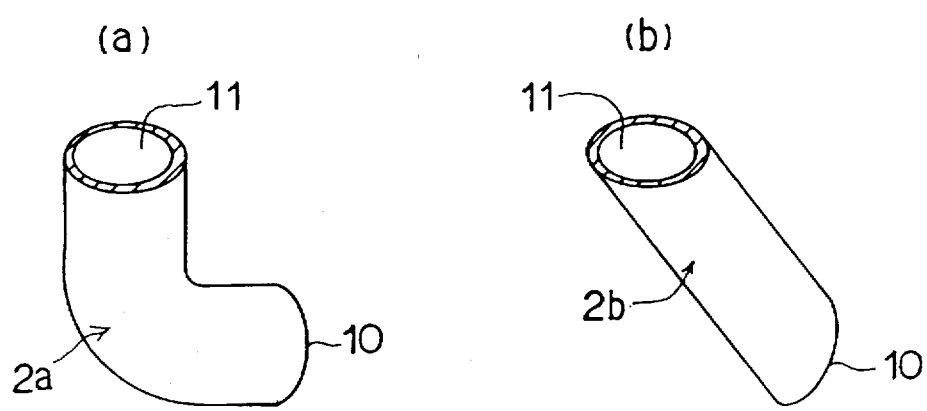
FIGS. 5 (a) and 5 (b) are schematic drawings showing another type of the centrifugal force generator.
Figure 6:
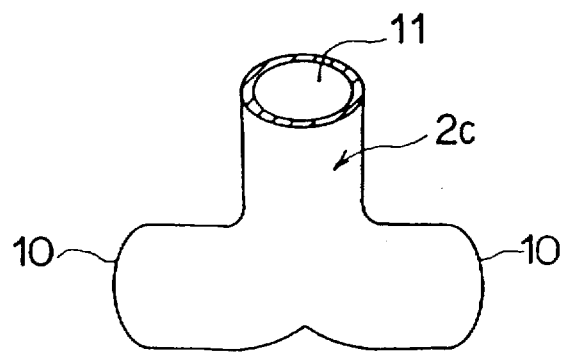
FIG. 6 is a schematic drawing showing another type of the centrifugal force generator.

On Figure 5, delete "(a)" and "(b)"; delete "Figure 5"; and, insert --Fig. 5(a)-- and --Fig. 5(b)--.

On Figure 6, delete "Figure 6" and insert --Fig. 6--.

On Figure 7, delete "Figure 7" and insert --Fig. 7--.

On Figure 8, delete "Figure 8" and insert --Fig. 8--.

On Figure 9, delete "Figure 9" and insert --Fig. 9--.

On Figure 10, delete "Figure 10" and insert --Fig. 10--.

On Figure 11, delete "Figure 11" and insert --FIG. 11--.

On Figure 12, delete "Figure 12" and insert --FIG. 12--.

On Figure 13, delete "Figure 13" and insert --FIG. 13--.

UNITED STATES PATENT AND TRADEMARK OFFICE
CERTIFICATE OF CORRECTION

PATENT NO. : 5,753,110
DATED : May 19, 1998
INVENTOR(S) : Masatoshi Matsumura et al.

Figure 14:
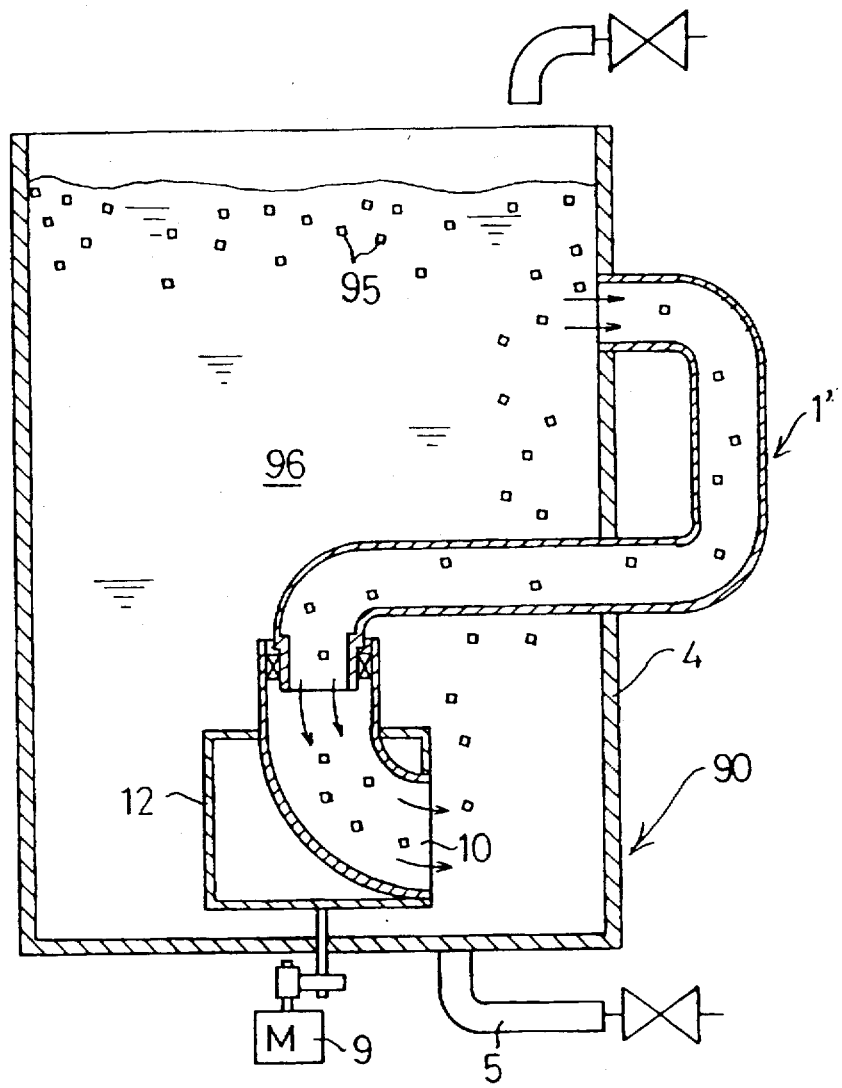
FIG. 14 is a sectional view showing an embodiment in which the fluid guide partly protrudes from the vessel.

It is certified that error appears in the above-identified patent and that said Letters Patent is hereby corrected as shown below:

On Figure 14, delete "Figure 14" and insert --FIG. 14--.

On Figure 15, delete "Figure 15" and insert --FIG. 15--.

On Figure 16, delete "Figure 16" and insert --FIG. 16--.

On Figure 17, delete "Figure 17" and insert --FIG. 17--.

On Figure 18, delete "Figure 18" and insert --FIG. 18--.

On Figure 19, delete "Figure 19" and insert --FIG. 19--.

On Figure 20, delete "Figure 20" and insert --FIG. 20--.

On Figure 21, delete "Figure 21" and insert --FIG. 21--.

On Figure 22, delete "Figure 22" and insert --FIG. 22--.

On Figure 23, delete "Figure 23" and insert --FIG. 23--.

Figure 24:
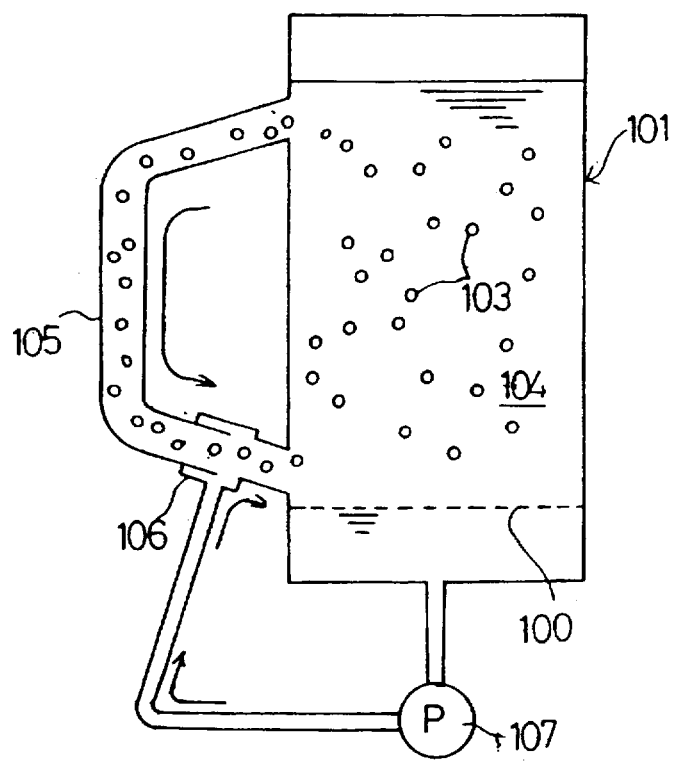
FIG. 24 is a sectional view showing a conventional biochemical reactor of liquid current type.

On Figure 24, delete "Figure 24" and insert --FIG. 24--.

On Figure 25, delete "Figure 25" and insert --FIG. 25--.

On Figure 26, delete "Figure 26" and insert --FIG. 26--.

At column 1, bridging lines 37 and 38, please delete "fertilizes" and insert --fertilizer--.

At column 3, line 44, delete "and" immediately after "filter tanks,".

UNITED STATES PATENT AND TRADEMARK OFFICE
CERTIFICATE OF CORRECTION

PATENT NO. : 5,753,110
DATED : May 19, 1998
INVENTOR(S) : Masatoshi Matsumura et al.

It is certified that error appears in the above-identified patent and that said Letters Patent is hereby corrected as shown below:

At column 4, line 65, delete "of" immediately after "rotation because" and insert --it--.

At column 5, line 16, immediately after "(such as nitrogen)" delete "and" and insert --,--.

At column 6, line 22, delete ";" and insert --.-- immediately after "tandem".

At column 6, line 32, insert --an-- immediately after "results of".

At column 6, line 35, insert --an-- immediately after "results of".

At column 7, line 33, delete "microorganism" and insert --microorganisms--.

At column 8, line 40, delete "(10)" immediately preceding "or it may have".

At column 9, line 6, replace "FIG. 1" with --FIG. 11--.

At column 9, line 66, replace "FIG. 8" with --FIG. 16--.

At column 11, line 58, replace "mean" with --means--.

At column 12, line 37, insert ")" immediately following "(67)".

UNITED STATES PATENT AND TRADEMARK OFFICE
CERTIFICATE OF CORRECTION

PATENT NO. : 5,753,110
DATED : May 19, 1998
INVENTOR(S) : Masatoshi Matsumura et al.

It is certified that error appears in the above-identified patent and that said Letters Patent is hereby corrected as shown below:

In the claims

In claim 15 (column 14, line 8), delete "1 1" and insert --11--.

Signed and Sealed this

First Day of June, 1999

Attest:

Q. TODD DICKINSON

Attesting Officer

Acting Commissioner of Patents and Trademarks